United States Patent
Sato et al.

(10) Patent No.: US 9,524,846 B2
(45) Date of Patent: Dec. 20, 2016

(54) TARGET STRUCTURE AND X-RAY GENERATING APPARATUS

(75) Inventors: Yasue Sato, Machida (JP); Takao Ogura, Yokohama (JP); Kazuyuki Ueda, Tokyo (JP); Ichiro Nomura, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 201 days.

(21) Appl. No.: 14/237,605

(22) PCT Filed: Aug. 8, 2012

(86) PCT No.: PCT/JP2012/070715
§ 371 (c)(1),
(2), (4) Date: Feb. 7, 2014

(87) PCT Pub. No.: WO2013/031535
PCT Pub. Date: Mar. 7, 2013

(65) Prior Publication Data
US 2014/0177800 A1    Jun. 26, 2014

(30) Foreign Application Priority Data
Aug. 31, 2011    (JP) ................. 2011-189107

(51) Int. Cl.
*H01J 35/18* (2006.01)
*H01J 35/08* (2006.01)
*G01N 23/04* (2006.01)

(52) U.S. Cl.
CPC ............. *H01J 35/08* (2013.01); *G01N 23/04* (2013.01); *H01J 35/18* (2013.01);
(Continued)

(58) Field of Classification Search
CPC ................ H01J 2235/087; H01J 2235/088; H01J 2235/186; H01J 35/08; H01J 35/18
See application file for complete search history.

(56) References Cited

U.S. PATENT DOCUMENTS

| 5,148,462 A | 9/1992 | Spitsyn et al. ........... 378/143 |
| 6,690,765 B1 | 2/2004 | Miller |

(Continued)

FOREIGN PATENT DOCUMENTS

| CN | 1672635 A | 9/2005 |
| JP | 07-169422 A | 7/1995 |

(Continued)

OTHER PUBLICATIONS

U.S. Appl. No. 14/293,493, filed Jun. 2, 2014.
(Continued)

*Primary Examiner* — David J Makiya
*Assistant Examiner* — John Corbett
(74) *Attorney, Agent, or Firm* — Fitzpatrick, Cella, Harper & Scinto

(57) ABSTRACT

In a target structure according to the present invention, a target is provided on a central area of an insulating substrate, and a first conductive member for supplying a voltage to the target is provided on a peripheral area of the insulating substrate which is exclusive of an area overlapping the target and is not covered by the target, so that the first conductive member is in contact with and electrically connected to the peripheral portion of the target. Consequently, it is possible to easily form a voltage supply line to the target without preventing diffusion of a heat generated in the target to the substrate and while suppressing emission of an unnecessary X-ray.

28 Claims, 3 Drawing Sheets

(52) U.S. Cl.
    CPC ... *H01J 2235/087* (2013.01); *H01J 2235/088* (2013.01); *H01J 2235/186* (2013.01)

(56) References Cited

U.S. PATENT DOCUMENTS

| | | |
|---|---|---|
| 8,416,920 B2 | 4/2013 | Okumura et al. |
| 2010/0266097 A1* | 10/2010 | Okunuki et al. .................. 378/9 |
| 2011/0058655 A1* | 3/2011 | Okumura et al. ............ 378/143 |
| 2013/0016812 A1 | 1/2013 | Yanagisawa et al. |
| 2013/0230143 A1 | 9/2013 | Ueda et al. |
| 2013/0235975 A1 | 9/2013 | Tamura et al. |
| 2014/0140480 A1 | 5/2014 | Ogura et al. |
| 2014/0140486 A1 | 5/2014 | Yanagisawa et al. |
| 2014/0153695 A1 | 6/2014 | Yanagisawa et al. |

FOREIGN PATENT DOCUMENTS

| | | | |
|---|---|---|---|
| JP | 2002-343290 A | 11/2002 | |
| JP | 2002-352754 A | 12/2002 | |
| JP | 2008-077981 A | 4/2008 | |
| JP | 2011-77027 A | 4/2011 | |

OTHER PUBLICATIONS

U.S. Appl. No. 14/258,641, filed Apr. 22, 2014.
Korean Office Action issued in counterpart application No. 10-2014-7007907 dated Mar. 31, 2015, along with its English-language translation (9 pages).
Japanese Office Action in corresponding Japanese Application No. 2011-189107 dated Jun. 30, 2015 (5 pages).
Chinese Office Action issued in counterpart application No. 201280041540.3 dated Jul. 21, 2015, along with its English language translation—13 pages.

* cited by examiner

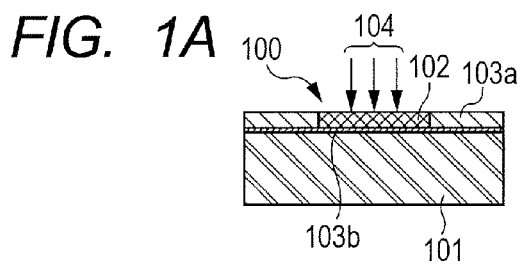 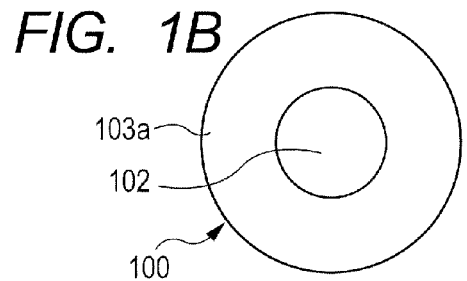
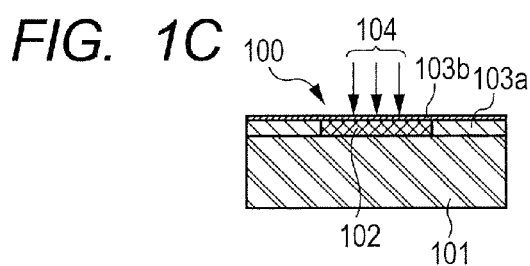 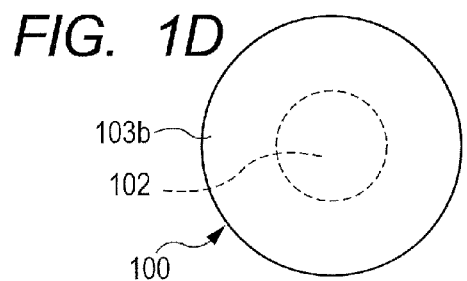
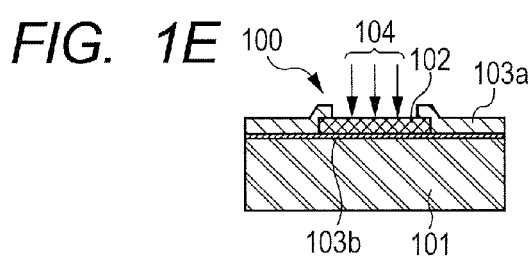 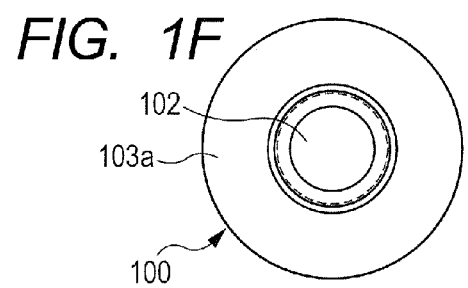
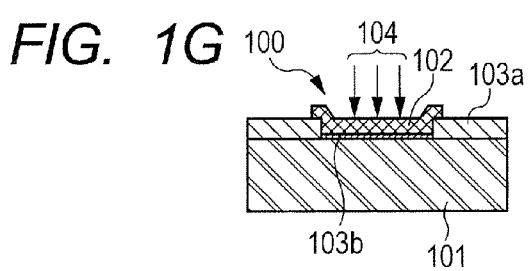 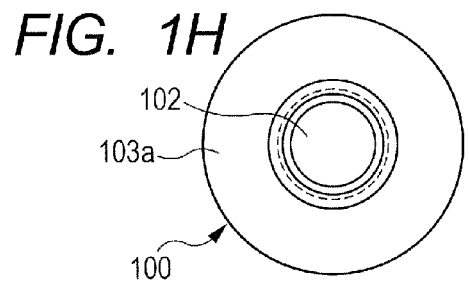
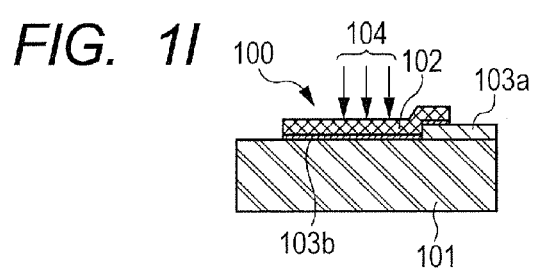 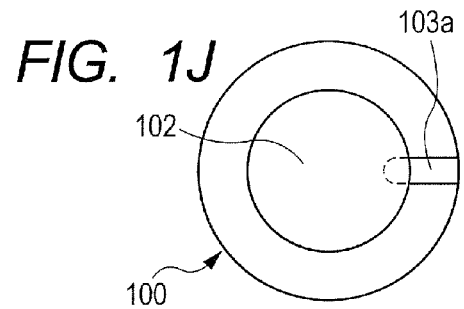

TARGET STRUCTURE AND X-RAY GENERATING APPARATUS

CROSS REFERENCE TO RELATED APPLICATION

The present application is a national-stage entry under 35 U.S.C. §371 of International Application No. PCT/JP2012/070715 filed on Aug. 8, 2012, and claims the benefit of foreign priority under 35 U.S.C. §119 of Japanese Application No. 2011-189107 filed on Aug. 31, 2011. Each of those applications is incorporated herein in its entirety, as if set forth fully herein.

TECHNICAL FIELD

The present invention relates to a target structure which generates an X-ray in response to irradiation of an electron beam, and an X-ray generating apparatus in which the target structure is used.

BACKGROUND ART

Conventionally, as a target structure, there has been known a structure in which an antistatic layer composed of a metal different from a target is formed on an insulating substrate composed of ceramics or glass materials and the target is formed on the relevant antistatic layer (e.g., PTL 1).

Moreover, there has been known a target substrate in which a conductive-material coating hardly generating an unnecessary X-ray is narrowly formed as a conductive lead to apply an accelerating voltage to a target buried in an anode base substrate made by synthetic diamond (e.g., PTL 2).

CITATION LIST

Patent Literature

PTL 1: Japanese Patent Application Laid-Open No. 2002-352754
PTL 2: Japanese Patent Application Laid-Open No. H07-169422

SUMMARY OF INVENTION

Technical Problem

However, in the target substrate described in PTL 1, since the antistatic layer is interposed between the target and the substrate, there is a problem that diffusion of heat generated in the target to the substrate is easily prevented.

Incidentally, when the conductive-material coating is formed on the electron beam irradiated area of the target, there is a problem that performance as an X-ray source is degraded because an unnecessary X-ray is generated from the formed conducive-material coating. In the target structure described in PTL 2, although it is intended to suppress generation of the unnecessary X-ray due to the conductive lead, there is a problem that restrictions on a process of forming the conductive lead and an arrangement of the conductive lead itself are increased.

The present invention, which has been completed in consideration of the above problems, aims to facilitate the diffusion of the heat generated in the target to the substrate, and also to be able to easily form the voltage supply line to the target while suppressing emission of the unnecessary X-ray.

Solution to Problem

In order to achieve such an object as described above, the present invention is to provide a target structure which is equipped with an insulating substrate and a target provided on one surface of the insulating substrate, wherein the target is provided on a central area of the insulating substrate, and a first conductive member for supplying a voltage to the target is provided on a part of a peripheral area of the insulating substrate which is exclusive of an area overlapping with a central portion of the target and is not covered by the target, so that the provided first conductive member is connected to the target.

Advantageous Effects of Invention

In the present invention, since the first conductive member is not provided on the central portion of the target to which an electron beam is irradiated, it is possible to suppress generation of an unnecessary X-ray due to the irradiation of the electron beam to the first conductive member. Therefore, it is unnecessary to specifically select, as the first conductive member, a material which does not generate an X-ray, and it is possible to provide the first conductive member on the peripheral area of the substrate in an arbitrary width, whereby a restriction concerning an arrangement of the voltage supply line to the target is small.

Moreover, in the present invention, it is possible by the first conductive member to supply a voltage to the target and prevent so-called charge-up without interposing another conductive member between the target and the substrate. Therefore, since heat energy can be transported well from the target to the substrate, it is possible to have well linearity in the X-ray emission and well output stability.

Moreover, in the present invention, it is possible by providing the second conductive member to stabilize the electrical connection state between the first conductive member and the target and thus improve adhesiveness of the target to the substrate.

Further features of the present invention will become apparent from the following description of exemplary embodiments with reference to the attached drawings.

BRIEF DESCRIPTION OF DRAWINGS

FIGS. 1A, 1B, 1C, 1D, 1E, 1F, 1G, 1H, 1I and 1J are schematic diagrams illustrating target structures according to the present invention.

DESCRIPTION OF EMBODIMENTS

Embodiment 1

Figure 2:
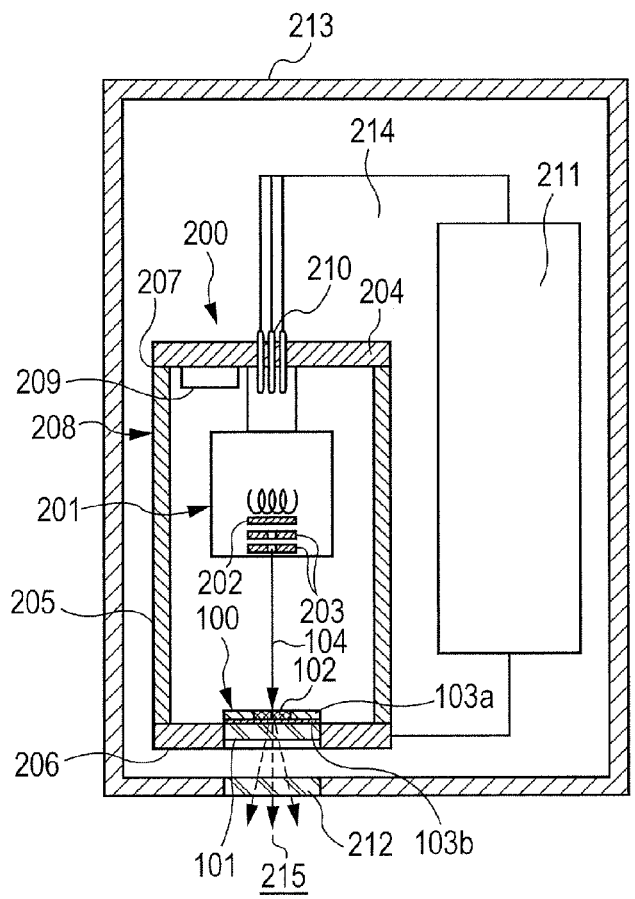
FIG. 2 is a schematic diagram illustrating a transmission-type X-ray generating apparatus according to the present invention.

FIGS. 1A and 1B are respectively a cross-sectional view and a plan view indicating a target structure 100 according to the embodiment 1 of the present invention. A second conductive member 103b is provided at the target structure 100 with such a state of crossing over both a central area and a peripheral area on one surface of a substrate 101, and a target 102 is provided on the second conductive member 103b in the central area of the substrate 101. A first conductive member 103a is provided on the second conductive member 103b in the peripheral area of the substrate 101 not covered with the target 102. That is, it is formed that the second conductive member 103b covers a lower surface side of the target 102 and is also extended to an area overlapped with the first conductive member 103a in the peripheral area of the substrate 101. The first conductive member 103a is formed in an area excepting an area overlapped with the target 102 with an electrically connected state by forming that an inner edge portion surface of the first conductive member 103a contacts with a peripheral side surface of the target 102.

A thickness of the first conductive member 103a is selected from a thickness range capable of easily supplying the necessary voltage to the target 102. The second conductive member 103b is provided with such a thickness equal to or less than 0.1 μm, and it can be also omitted. However, when the second conductive member 103b is provided, since it is formed as so-called an underlayer crossing over both the first conductive member 103a and the target 102, an electrical connection between the first conductive member 103a and the target 102 can be stabilized. In addition, adhesiveness of the target 102 to the substrate 101 can be increased by the presence of the second conductive member 103b, which serves as the underlayer of the target 102. Even if the second conductive member 103b lies between the substrate 101 and the target 102, the heat diffusion of the target 102 to the substrate 101 is not prevented by providing the second conductive member 103b to have such a thickness equal to or less than 0.1 μm. From the viewpoint of obtaining stability in the electrical connecting condition and improvement in the adhesiveness of the target 102 to the substrate 101, it is preferable that a thickness of the second conductive member 103b is equal to or larger than 0.1 nm.

The target 102 generates an X-ray by receiving the irradiation of an electron beam 104. As materials of the target 102, for example, W, Cu, Ta, Pt, Mo, Te and the alloy thereof are preferable. Also, according to other needs, the materials can be selected from conductive members (metal, alloy, semiconductor or the like). Almost energy held by the electron beam 104 is transformed into the heat energy, and a temperature of the target 102 is increased to the high temperature (equal to or higher than several hundred degrees). The heat generated at the target 102 conducts to the substrate 101 to increase the temperature of the substrate 101. The substrate 101 is required to have electrical insulation, heat resistance and excellent heat conductivity, and, for example, the material such as ceramics, diamond, glass or like is preferably used. In addition, in case of forming a transmission-type target structure which radiates an X-ray to the outside through the substrate 101, it is preferable to select the material, thickness thereof and the like so that the generated X-ray is not greatly attenuated.

As materials of the first conductive member 103a and the second conductive member 103b, for example, a metal such as Ti, Ta or the like is preferable. However, according to other needs, the materials can be selected from a conductive metal (includes alloy). In addition, both the same material and different materials are available for the first conductive member 103a and the second conductive member 103b.

The height from a surface of the substrate 101 to a surface of the first conductive member 103a is equal to the height from the surface of the substrate 101 to a surface of the target 102.

Embodiment 2

FIGS. 1C and 1D are respectively a cross-sectional view and a plan view indicating a target structure 100 according to the embodiment 2 of the present invention. A target 102 and a first conductive member 103a are directly provided on one surface of a substrate 101, and a second conductive member 103b is provided on the target 102 and the first conductive member 103a. The embodiment 2 is similar to the above-mentioned embodiment 1 excepting the above points.

The electrical connecting condition between the target 102 and the first conductive member 103a can be stabilized by a fact that the second conductive member 103b is formed on upper surfaces of the target 102 and the first conductive member 103a with such a state of crossing over both of them. Although the second conductive member 103b covers an upper surface side of the target 102, generation of unnecessary X-rays can be suppressed even if receiving an irradiation of the electron beam 104 by a fact that a thickness of the second conductive member 103b is equal to or less than 0.1 μm. In addition, the second conductive member 103b can be also omitted similar to a case of the embodiment 1, However, from the viewpoint of obtaining stability in the electrical connecting condition, it is preferable that a thickness of the second conductive member 103b is set to become equal to or larger than 0.1 nm.

Embodiment 3

FIGS. 1E and 1F are respectively a cross-sectional view and a plan view indicating a target structure 100 according to the embodiment 3 of the present invention. The embodiment 3 is almost similar to the embodiment 1 excepting a point that an inner edge portion of a first conductive member 103a is overlapped with a peripheral portion of a target 102. That is, the first conductive member 103a, of which an inner edge portion is overlapped with the peripheral portion of the target 102, is connected with the target 102 and is formed in an area excepting a central portion of the target 102. By adopting this structure, an electrical connection between the target 102 and the first conductive member 103a can be more ensured easily. Generally, since the electron beam 104 is irradiated to a center portion of the target 102, if a portion, where the inner edge portion of the first conductive member 103a is overlapped, is just on the peripheral portion of the target 102, generation of unnecessary X-rays due to the irradiation of the electron beam 104 can be suppressed. A second conductive member 103b is not fixed to an entire one surface of the substrate 101 but is fixed to the substrate 101 from a portion overlapped with the target 102 to an intermediate portion of a peripheral area of the substrate 101 not covered with the target 102 with an extended state. By adopting this structure, a formation area of the second conductive member 103b can be reduced to a small size, and adhesiveness between the target 102 and the substrate 101 can be improved and an electrical connecting condition between the target 102 and the first conductive member 103a can be stabilized.

Embodiment 4

FIGS. 1G and 1H are respectively a cross-sectional view and a plan view indicating a target structure 100 according to the embodiment 4 of the present invention. The embodiment 4 is almost similar to the embodiment 1 excepting a point that a peripheral portion of a target 102 is overlapped with an inner edge portion of a first conductive member 103a. That is, the first conductive member 103a is electrically connected with the target 102 by forming that a peripheral portion of the target 102 is overlapped with an inner edge portion of the first conductive member 103a and is formed in an area excepting a central portion of the target 102. By adopting this structure, an electrical connection between the target 102 and the first conductive member 103a can be more ensured easily. In addition, since the inner edge portion of the first conductive member 103a is only overlapped with the peripheral portion of the target 102, the heat of the target 102 is not almost prevented to be transmitted to the substrate 101. In addition, a second conductive member 103b, of which the material is different from that of the first conductive member 103a, is provided only in an area which corresponds to the target 102. In case of providing the second conductive member 103b in order to improve adhesiveness of the target 102 to the substrate 101 as a main object, the second conductive member 103b is provided in such a range as mentioned above, thereby realizing to suppress the size of this range, which is required for forming the second conductive member 103b, to a small size.

Embodiment 5

FIGS. 1I and 1J are respectively a cross-sectional view and a plan view indicating a target structure 100 according to the embodiment 5 of the present invention. The embodiment 5 is almost similar to the embodiment 4 excepting a point that a first conductive member 103a is provided in a part of a peripheral area of a substrate 101 not covered with a target 102. A formation area of the first conductive member 103a can be selected based on such a range necessary for giving voltage to the target 102. Although the first conductive member 103a is provided at one position, the first conductive members 103a can be provided at several positions separately. For example, several pieces can be provided in the radiating direction. In addition, it can be also formed that a second conductive member 103b is extended to both a peripheral area of the substrate 101 overlapped with the first conductive member 103a at the same time and a peripheral area of the substrate 101 not covered with the first conductive member 103a at the same time.

Embodiment 6

Next, an X-ray generating apparatus using a target structure according to the present invention will be described. FIG. 2 is a schematic diagram indicating a transmission-type X-ray generating apparatus which extracts an X-ray to the direction identical with a traveling direction of an electron beam 104. First, an X-ray generating tube 200 will be described. A metallic electron gun flange 204, a cylindrical insulator 205 and a metallic anode unit 206 are mutually vacuum-tightly bonded at their bonding portions 207 to form an envelope 208 which can be decompressed. The glass or ceramics are preferably used for the insulator 205, and alumina is preferably used in point of insulation property, vacuum airtightness, heat conductivity and wettability with metal. As the material of the electron gun flange 204, a Kovar is optimally used in a case that the insulator 205 is the alumina, and quality of the material of the electron gun flange 204 is determined in consideration of quality of the material of the insulator 205. As a method of vacuum-tight bonding, a brazing method is preferable.

An electron emitting source (electron gun) 201 is located at the electron gun flange 204. The electron emitting source 201 makes a cathode 202 emit electrons, and the electrons emitted from the cathode 202 are formed into the electron beam 104 having desired orbit and size at a controlling electrode 203, and the electron beam 104 is emitted toward the target 102. As the cathode 202, a filament-type cathode using a high melting point metal such as tungsten, rhenium or the like or obtained by applying yttria or the like on a surface of the above-mentioned metal, a thermal field emission type cathode and an impregnated cathode obtained by impregnating BaO with the porous tungsten as a main component can be adapted. In addition, a cold cathode or the like represented by a Spindt-type cold cathode, a carbon nanotube or a surface conduction type cold cathode is also can be adapted. The power and electric signals required to drive the electron emitting source 201 are generated by a driving power source unit 211 and are supplied from an external portion through a vacuum-tight current/voltage introduction unit 210 fixed to the electron gun flange 204.

The anode unit 206 is located facing the electron emitting source 201. The target structure 100 according to each of the embodiments 1 to 5 is vacuum-tightly bonded to an opening formed in the anode unit 206. The substrate 101 of the target structure 100 is bonded to a wall surface of the opening. In a case that the material of the substrate 101 is alumina, as the material of the anode unit 206 excepting the target structure 100, Kovar having a thermal expansion coefficient similar to that of the alumina is preferable. In a case that the thermal expansion coefficients of the insulator 205 and the substrate 101 are greatly different from each other, not only one kind of metal but metals, of which thermal expansion coefficients are nearly identical with each other, are vacuum-tightly bonded, thereafter those metals can be vacuum-tightly bonded to each other. As a method of the vacuum-tight bonding performed between the above-mentioned metals, a brazing method or the welding is preferable. The driving power source unit 211 generates acceleration voltage used for accelerating the electron beam 104 and applies that voltage to the anode unit 206. Therefore, the driving power source unit 211 is electrically connected with the anode unit 206, and in addition, the target 102 is electrically connected with the driving power source unit 211 through the first conductive member 103a (and second conductive member 103b) electrically connected with the anode unit 206.

The inside of the envelope 208 is maintained to be a vacuum state by a getter 209. As the getter 209, a vapor deposition getter using Ba or a non-vapor deposition getter consisted of an alloy composed of Zr, Ti, V, Fe, Al and the like can be used.

The transmission-type X-ray generating apparatus has the X-ray generating tube 200 and the driving power source unit 211 which are located inside a container 213. An extra space inside the container 213 is filled with an insulating oil 214 to secure the withstand voltage, and an outer window 212 used for extracting X-rays 215 to the outside of the container 213 is fixed to a position facing the substrate 101 in the container 213.

The electron beam 104 emitted from the electron emitting source 201 is further accelerated by the voltage applied to the anode unit 206 and collides with the target 102 of the target structure 100, then a part of the energy is radiated as the X-ray. The X-ray is extracted to the outside through the insulating substrate 101, the insulating oil 214 and the outer window 212. However, almost all of the residual energy is transformed into the thermal energy at the target 102.

Embodiment 7

Figure 3:
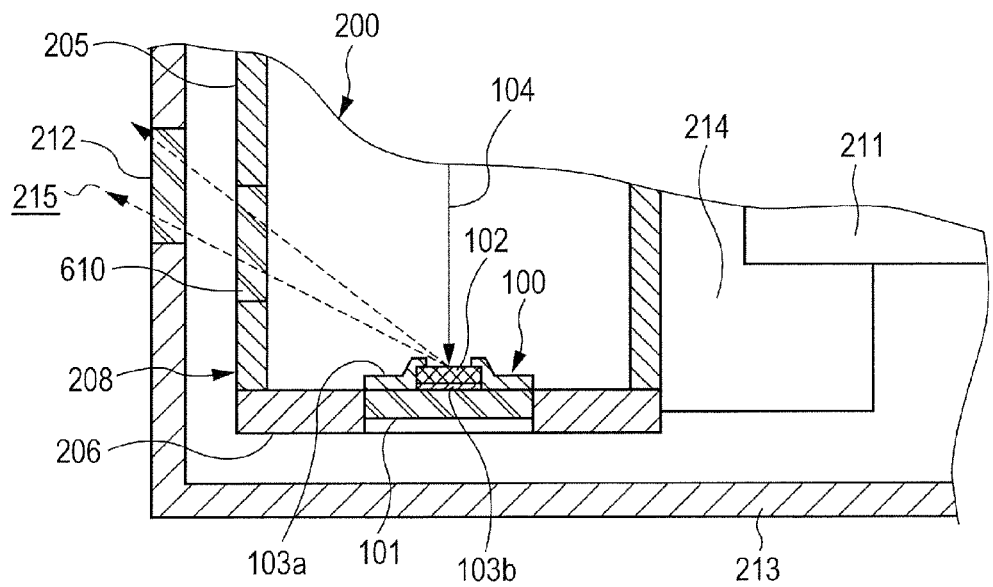
FIG. 3 is a partial schematic diagram illustrating a reflection-type X-ray generating apparatus according to the present invention.

FIG. 3 is a schematic diagram indicating a reflection-type X-ray generating apparatus using the target structure according to the present invention. The X-ray 215 is extracted from the direction different from the traveling direction of the electron beam 104. In this embodiment, the target structure 100 according to each of the first to fifth embodiments is used. The target structure 100 is fixed to an anode 206 which does not have an opening, and an X-ray window 610 used for extracting X-rays from an envelope 208 is provided at an insulator 205. An outer window 212 provided at a container 213 is provided at such a position which does not face a substrate 101 but face the X-ray window 610.

Embodiment 8

Figure 4:
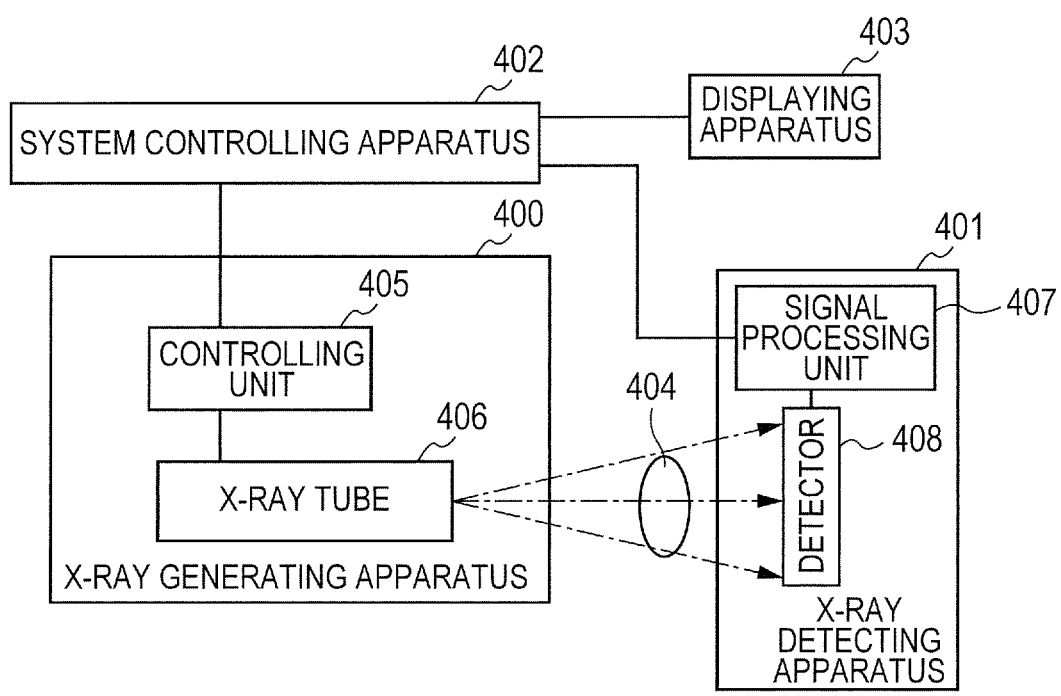
FIG. 4 is a schematic diagram illustrating an X-ray photography system according to the present invention.

FIG. 4 is a block diagram of an X-ray photography system according to the present invention. A system controlling apparatus 402 cooperatively controls an X-ray generating apparatus 400 and an X-ray detecting apparatus 401. A controlling unit 405 outputs various control signals to an X-ray tube 406 under the control of the system controlling apparatus 402. The emitting condition of an X-ray to be emitted from the X-ray generating apparatus 400 is controlled by the control signals. The X-ray emitted from the X-ray generating apparatus 400 transmits through a subject 404 to be detected at a detector 408. The detector 408 transforms the detected X-ray into an image signal and output the image signal to a signal processing unit 407. The signal processing unit 407 performs a predetermined signal processing to the image signal under the control of the system controlling apparatus 402 and outputs the processed image signal to the system controlling apparatus 402. The system controlling apparatus 402 outputs a display signal, which is used for displaying an image on a displaying apparatus 403, to the displaying apparatus 403 on the basis of the processed image signal. The displaying apparatus 403 displays an image based on the display signal on a screen as a photography image of the subject 404.

Example 1

First, the electron emitting source 201 indicated in FIG. 2 was fabricated. As the cathode 202, an impregnated cathode composed of BaO as a main component was used. And, as the controlling electrode 203, molybdenum electrodes formed by two electrodes having a passage hole, of which a diameter $\phi$ is 2 mm, between them was used. The electron emitting source 201 was fixed to the electron gun flange 204, and in addition, the vacuum-tight voltage/current introduction unit 210 was connected with the electrodes of the electron emitting source 201. In addition, as the getter 209, a non-evaporation getter "ST172" produced by SAES Getters S.p.A. in Italy was located in the electron gun flange 204, and a heater built in the getter 209 was connected with the voltage/current introduction unit 210.

Next, the target structure 100 indicated in FIGS. 1A and 1B was fabricated. As the insulating substrate 101, "Sumicrystal™", which is an artificial diamond, produced by Sumitomo Electric Industries, Ltd. was used. As for the size thereof, a diameter is 5 mm and a thickness is 1 mm. As the second conductive member 103b, Ti was deposited on the substrate 101 to have a thickness of 0.05 μm by a sputtering method. As the target 102, W was formed in a central area of the substrate 101 on the second conductive member 103b to have such a size, of which a diameter is 3 mm and a thickness is 10 μm, by a sputtering method of using a mask. In addition, as the first conductive member 103a, Ti was deposited on a peripheral area of the substrate 101 not covered by the target 102 to have a thickness of 0.05 μm by the sputtering method of using a mask similarly.

Next, the anode unit 206 was fabricated. First, a metallizing process was performed to a side surface portion of the substrate 101, on which the target 102 was formed, by using a metal paste. Next, as for the anode unit 206, a main part thereof is a Kovar, of which a diameter $\phi$ is 50 mm, and the target structure 100 was brazed at a center of the anode 206 at a high temperature of 850° C. in the vacuum space by using the brazing material "BA-108" produced by Toyo Riken Co., Ltd. and was vacuum-tightly bonded.

Next, the insulator 205 was fabricated. The material of the insulator 205, which has a cylindrical shape of which a diameter $\phi$ is 50 mm and a thickness is 4 mm, is alumina. A metallizing process was performed to both ends of the insulator 205 by using a metal paste.

Next, the electron gun flange 204, in which the electron emitting source 201 and the like are located, the anode unit 206, where the target structure 100 is located, and the insulator 205 were put into a vacuum furnace, where they were brazed each other at a low temperature. A low temperature brazing process was performed at a temperature of 700° C. in the vacuum atmosphere by using the brazing material "BA-143" produced by Toyo Riken Co., Ltd., and an X-ray generating apparatus, in which the envelope 208 indicated in FIG. 2 is located, was fabricated. At this time, a copper pipe (not illustrated), of which a diameter $\phi$ is ¼ inch, was brazed at the electron gun flange 204 by using the brazing material "BA-143" at the same time. In addition, a small amount of the brazing material "BA-143" was put between the anode unit 206 and a part of the first conductive member 130a then this brazing material was melted to get the conduction between them.

Next, the above-mentioned copper pipe was connected with an evacuation system (not illustrated), and a vacuum heating degassing process was performed by baking the envelope 208 at 400° C. while vacuum exhausting the inside of the envelope 208. In addition, a driving power source unit (not illustrated) was connected with the voltage/current introduction unit 210, and a filament of the electron emitting source 201 was heated, then the cathode 202 was activated. Next, a voltage applying means (not illustrated) was connected with the anode unit 206 to apply the voltage of 1 kV, and then an electron beam 104 of 10 mA was made to be collided with the target 102 from the electron emitting source 201, and the 48 hours aging test was performed. Subsequently, after a current was applied to the getter 209 to perform activation at 600° C., the above-mentioned copper pipe was chipped off, and the X-ray generating tube 200 was fabricated.

Next, the X-ray generating tube 200 was located in the container 213 filled with an insulating oil, then the voltage/current introduction unit 210 was connected with the driving power source unit 211, and the anode unit 206 was connected with the driving power source unit 211 at the same time. At the end, the container 213 was sealed to complete the fabrication of the X-ray generating apparatus.

In order to measure the X-ray amount, an ion-chamber type dosimeter (2186 dosimeter and ion chamber "10×6-180") produced by the U.S. Radcal Corporation was located on a position apart from the substrate 101, which serves as an X-ray transmissive window, by 1 m. In addition, the voltage of 100 kV was applied to the anode unit 206, and the X-ray generating apparatus was adjusted so that a focus size on the target 102 becomes such a size, of which a diameter ϕ is equal to 1 mm, within a range of the current density from 1 mA/mm$^2$ to 20 mA/mm$^2$.

First, the current density of the electron beam 104 was made to be changed and then linearity of the X-ray amount to be radiated was measured. The voltage to be applied to the anode unit 206 was fixed to become 100 kV, and the current density was made to be changed from 1.0 mA/mm$^2$ to 5.0 mA/mm$^2$ and to 20.0 mA/mm$^2$, and the X-ray amount radiated at that time was measured by the above-mentioned dosimeter. When the current density was 1.0 mA/mm$^2$, the X-ray amount was about 0.3 mR/h. The linearity of the X-ray amount was evaluated on the basis of the current density 1.0 mA/mm$^2$ of the electron beam 104. The evaluated result will be indicated in Table 1.

There was no problem because of not generating a charge-up phenomenon and almost not detecting a gap from the linearity even if the temperature of the target 102 was risen. Next, the stability was evaluated. The current density of the electron beam 104 was kept to become constant density at a level of 10.0 mA/mm$^2$, and also the voltage to be applied to the anode unit 206 was kept to become constant voltage at a level of 100 kV, and then a temporal change of the X-ray amount was measured. The measured result will be indicated in Table 1. Even after the elapse of 50 hours, the X-ray amount was in a stable state without almost changing the amount, and it was confirmed to indicate the excellent stability. In the evaluation indicated in Table 1, a mark "○" denotes an excellent result.

Example 2

First, the target structure 100 indicated in FIGS. 1E and 1F was fabricated. As the insulating substrate 101 in these diagrams, "Sumicrystal™", which is an artificial diamond, produced by Sumitomo Electric Industries, Ltd. was used. As for the size thereof, a diameter is 5 mm and a thickness is 1 mm. As the second conductive member 103*b*, Ti was deposited on an entire one surface of the substrate 101 to have a thickness of 0.05 μm by a sputtering method. As the target 102, W was deposited on a central area of the substrate 101 on the second conductive member 103*b* to have such a size, of which a diameter ϕ is 4 mm and a thickness is 10 μm, by a sputtering method of using a mask. In addition, as the first conductive member 103*a*, a hole of which a diameter ϕ is just 3 mm was formed in a central portion by using a mask and then Ti was deposited to have a thickness of 0.095 μm by a sputtering method. In this example, the target 102, which is exposed at a central portion, is overlapped with the first conductive member 103*a* at a peripheral portion of the target 102.

Next, the envelope 208 was fabricated similar to a case of the example 1 by using the target structure 100. In addition, the X-ray generating tube 200 was fabricated by performing a vacuum baking process, an aging test and a chip-off process similar to the case of the example 1. Next, the X-ray generating tube 200 was located in the container 213, and the X-ray generating apparatus was fabricated similar to the case of the example 1.

Next, the linearity and stability were measured similar to the case of the example 1. The measured results will be indicated in Table 1. There was no problem because of not generating a charge-up phenomenon and almost not detecting a gap from the linearity even if the temperature of the target 102 was risen. Even after the elapse of 50 hours, the X-ray amount did not almost change, and it was confirmed to have an excellent stability.

In addition, a spectrum of an X-ray to be emitted was measured by a semiconductor detector produced by the U.S. AMPTEK Corporation. The amount of a characteristic X-ray (4.5 keV, 4.9 keV) from Ti, which is a component of the second conductive member 103*b*, was at a level less than 0.1%, and this result brought about no problem.

Example 3

First, the target structure 100 indicated in FIGS. 1G and 1H was fabricated. As the insulating substrate 101 in these diagrams, "Sumicrystal™", which is an artificial diamond, produced by Sumitomo Electric Industries, Ltd. was used. As for the size thereof, a diameter is 5 mm and a thickness is 1 mm. As the second conductive member 103*b*, Ti, of which a diameter ϕ is 3 mm, was deposited on a central area of the substrate 101 to have a thickness of 0.095 μm by a sputtering method of using a mask. Next, Mo was deposited on a peripheral area of the substrate 101, which is a circumferential area of the second conductive member 103*b*, to have a thickness of 1 μm by a sputtering method by using a mask, thus the first conductive member 103*a* was formed. In addition, as the target 102, W was deposited to have such a size, of which a diameter ϕ is 4 mm and a thickness is 10 μm, by using a mask. The target 102 was formed to overlap with the first conductive member 103*a* at a peripheral portion of the target 102.

Next, the envelope 208 was fabricated by using the target structure 100 similar to the case of the example 1. In addition, the X-ray generating tube 200 was fabricated by performing a vacuum baking process, an aging test and a chip-off process similar to the case of the example 1. Next, the X-ray generating tube 200 was located in the container 213 similar to the case of the example 1, and the fabrication of the X-ray generating apparatus was completed.

Next, the linearity and stability were measured similar to the case of the example 1. The measured results will be indicated in Table 1. There was no problem because of almost not detecting a gap from the linearity even if the temperature of the target 102 was risen. Even after the elapse of 50 hours, the X-ray amount did not almost change, and it was confirmed to have an excellent stability.

Example 4

First, the target structure 100 indicated in FIGS. 1I and 1J was fabricated. As the insulating substrate 101, "Sumicrystal™", which is an artificial diamond, produced by Sumitomo Electric Industries, Ltd. was used. As for the size thereof, a diameter is 5 mm and a thickness is 1 mm. The first conductive member 103*a* made of Mo was fabricated to have such a size, of which a width is 1 mm, a length is 1.3 mm and a thickness is 1 μm, on such a position, which is from the periphery of the substrate 101 to the intermediate point in the course of approaching to a center of the substrate 101, by a sputtering method of using a mask. Next, as the second conductive member 103*b*, Ti, of which a diameter ϕ is 3 mm, was deposited on a central area of the substrate 101 to have a thickness of 0.05 μm by using a mask. Next, as the target 102, W was deposited to have such a size, of which a diameter ϕ is 3 mm and a thickness is 10 μm, by using a mask. The second conductive member 103*b* made of Ti and the target 102 were formed on an inner edge portion of the first conductive member 103*a* made of Mo such that a peripheral portion of the second conductive member 103b is overlapped with a peripheral portion of the target 102.

Next, the envelope 208 was fabricated by using the target structure 100 similar to the case of the example 1. In addition, the X-ray generating tube 200 was fabricated by performing a vacuum baking process, an aging test and a chip-off process similar to the case of the example 1. Next, the X-ray generating tube 200 was located in the container 213, and the fabrication of the X-ray generating apparatus was completed similar to the case of the example 1.

The linearity and stability were measured similar to the case of the example 1. The measured results will be indicated in Table 1. There was no problem because of not generating a charge-up phenomenon and almost not detecting a gap from the linearity even if the temperature of the target 102 was risen. Even after the elapse of 50 hours, the X-ray amount did not almost change, and it was confirmed to have an excellent stability.

Example 5

First, the target structure 100 indicated in FIG. 3 was fabricated. As the insulating substrate 101 in this diagram, "Sumicrystal™", which is an artificial diamond, produced by Sumitomo Electric Industries, Ltd. was used. As for the size thereof, a diameter is 5 mm and a thickness is 1 mm. As the second conductive member 103b, Ti was deposited on a central area of the substrate 101 to have such a size, of which a diameter $\phi$ is 4 mm and a thickness is 0.05 μm, by a sputtering method by using a mask. As the target 102, W was deposited on the second conductive member 103b to have such a size, of which a diameter $\phi$ is 4 mm and a thickness is 10 μm, by using a mask. In addition, as the first conductive member 103a, a hole of which diameter $\phi$ is just 3 mm was formed in a central portion by using a mask and then Mo was deposited to have a thickness of 0.095 μm by a sputtering method. In the present example, an upper surface of the target 102 is exposed, and a peripheral portion of the target 102 is overlapped with the conductive member 103b. The present example indicates a reflection-type X-ray generating apparatus which radiates X-rays in the opposite direction to the traveling direction of the electron beam 104.

Next, a brazing process was performed to the anode unit 206, of which a portion where the substrate 101 is to be located is not opened toward the outside, by using the target structure 100 similar to the case of the example 1. Then, the envelope 208 indicated in FIG. 3 was fabricated by using the insulator 205, of which a part where the X-ray window 610 made of Be (beryllium) is located, and using the same members as those in the example 1 excepting the above-mentioned insulator 205. In addition, the X-ray generating tube 200 was fabricated by performing a vacuum baking process, an aging test and a chip-off process similar to the case of the example 1. Next, the X-ray generating tube 200 was located in the container 213, of which the X-ray outer window 212 was changed to form at another position, similar to the case of the example 1, and the fabrication of the X-ray generating apparatus was completed.

Next, the linearity and stability were measured similar to the case of the example 1. The measured results will be indicated in Table 1. There was no problem because of not generating a charge-up phenomenon and almost not detecting a gap from the linearity even if the temperature of the target 102 was risen. Even after the elapse of 50 hours, the X-ray amount did not almost change, and it was confirmed to have an excellent stability.

In addition, a spectrum of an X-ray to be emitted was measured by a semiconductor detector produced by the U.S. AMPTEK Corporation. The amount of a characteristic X-ray (17.5 keV, 19.6 keV) from Mo, which is a component of the second conductive member 103b, was at a level less than 0.3%, and this result brought about no problem.

TABLE 1

| | Linearity of X-ray amount | | | Stability of X-ray amount | | |
|---|---|---|---|---|---|---|
| | Gap from linearity (%) | | | Rate of variability to initial stage (%) | | |
| | | | | Elapse of 1 hour | Elapse of 50 hours | |
| | Current density 5.0 mA/mm² | Current density 20.0 mA/mm² | Evaluation | after starting measurement | after starting measurement | Evaluation |
| Example 1 | 0.41 | 0.44 | ○ | 0.22 | 0.31 | ○ |
| Example 2 | 0.42 | 0.43 | ○ | 0.33 | 0.38 | ○ |
| Example 3 | 0.48 | 0.47 | ○ | 0.39 | 0.41 | ○ |
| Example 4 | 0.40 | 0.38 | ○ | 0.33 | 0.32 | ○ |
| Example 5 | 0.41 | 0.39 | ○ | 0.32 | 0.34 | ○ |
| Measurement condition | Current density: comparison to 1.0 mA/mm² Focus size: $\phi$1.0 mm Voltage of anode: 100 kV | | | Current density: 1/0 mA/mm² Focus size: $\phi$1.0 mm Voltage of anode: 100 kV | | |

A mark "○" denotes an excellent result.

REFERENCE SIGNS LIST 100 target structure
101 substrate
102 target
103a first conductive member
103b second conductive member While the present invention has been described with reference to the exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-189107, filed Aug. 31, 2011, which is hereby incorporated by reference herein in its entirety.

The invention claimed is:

1. A target structure which is equipped with an electrically insulating substrate and a target provided on one surface of the electrically insulating substrate, wherein the target is provided on a central area of the electrically insulating substrate, wherein a first conductive member for supplying a voltage to the target is provided on a part of a peripheral area of the electrically insulating substrate which is exclusive of an area overlapping with a central portion of the target and is not covered by the target, so that the provided first conductive member is connected to the target, and wherein an inner edge portion of the first conductive member is overlapped with a peripheral portion of the target.

2. The target structure according to claim 1, wherein an inner edge portion of the first conductive member is in contact with a peripheral side surface of the target.

3. The target structure according to claim 1, wherein a second conductive member of which a thickness is 0.1 μm or less is provided so as to cover at least a part of either one of an upper surface and a lower surface of the target and so as to be connected to the first conductive member.

4. The target structure according to claim 3, wherein the thickness of the second conductive member is 0.1 nm or more.

5. The target structure according to claim 3, wherein the second conductive member is formed so as to extend in an area, on a peripheral area of the electrically insulating substrate, overlapping the first conductive member.

6. The target structure according to claim 5, wherein the first conductive member is provided on a part of the peripheral area of the electrically insulating substrate, and wherein the second conductive member is formed so as to extend in the area, on the peripheral area of the electrically insulating substrate, overlapping with the first conductive member and in an area, on the peripheral area of the electrically insulating substrate, not covered by the first conductive member.

7. An X-ray generating apparatus which is equipped with an electron emitting source and a target structure having a target on a side facing the electron emitting source, wherein the target structure is the target structure according to claim 1.

8. An X-ray photography system comprising:
the X-ray generating apparatus according to claim 7;
an X-ray detecting apparatus which detects an X-ray emitted from the X-ray generating apparatus and transmitted through a subject; and
a controlling apparatus which controls the X-ray generating apparatus and the X-ray detecting apparatus so that the X-ray generating apparatus and the X-ray detecting apparatus cooperate with each other.

9. A target structure which is equipped with an electrically insulating substrate and a target provided on one surface of the electrically insulating substrate, wherein the target is provided on a central area of the electrically insulating substrate, wherein a first conductive member for supplying a voltage to the target is provided on a part of a peripheral area of the electrically insulating substrate which is exclusive of an area overlapping with a central portion of the target and is not covered by the target, so that the provided first conductive member is connected to the target, and wherein a second conductive member of which a thickness is 0.1 μm or less is provided so as to cover at least a part of either one of an upper surface and a lower surface of the target and so as to be connected to the first conductive member.

10. The target structure according to claim 9, wherein an inner edge portion of the first conductive member is in contact with a peripheral side surface of the target.

11. The target structure according to claim 9, wherein the thickness of the second conductive member is 0.1 nm or more.

12. The target structure according to claim 9, wherein the second conductive member is formed so as to extend in an area, on a peripheral area of the electrically insulating substrate, overlapping the first conductive member.

13. The target structure according to claim 12, wherein the first conductive member is provided on a part of the peripheral area of the electrically insulating substrate, and wherein the second conductive member is formed so as to extend in the area, on the peripheral area of the electrically insulating substrate, overlapping with the first conductive member and in an area, on the peripheral area of the electrically insulating substrate, not covered by the first conductive member.

14. An X-ray generating apparatus which is equipped with an electron emitting source and a target structure having a target on a side facing the electron emitting source, wherein the target structure is the target structure according to claim 9.

15. An X-ray photography system comprising:
the X-ray generating apparatus according to claim 14;
an X-ray detecting apparatus which detects an X-ray emitted from the X-ray generating apparatus and transmitted through a subject; and
a controlling apparatus which controls the X-ray generating apparatus and the X-ray detecting apparatus so that the X-ray generating apparatus and the X-ray detecting apparatus cooperate with each other.

16. A transmitting type target comprising:
an electrically insulating substrate having a pair of surfaces facing each other and an annular lateral periphery coupled with each of the pair of surfaces;
a target located on one of the pair of surfaces and located at internal region internally spaced apart from the annular lateral periphery; and
a first conductive member located on the one of the pair of surfaces and having an inner edge portion being overlapped to a peripheral of the target so as to be electrically connected to the target.

17. The transmitting type target according to claim 16, further comprising a second conductive member provided on or underneath the target, wherein the second conductive member has a thickness of 0.1 μm or less.

18. The transmitting type target according to claim 17, wherein the thickness of the second conductive member is 0.1 nm or more.

19. The transmitting type target according to claim 17, wherein the second conductive member overlaps the first conductive member.

20. The transmitting type target according to claim 19, wherein the second conductive member is located between the target and the one of the pair of surfaces of the electrically insulating substrate.

21. An X-ray generating apparatus comprising the transmitting type target according to claim 16 and an electron emitting source facing the transmitting type target.

22. A radiography system comprising:
the X-ray generating apparatus according to claim 21;
an X-ray detecting apparatus which detects an X-ray emitted from the X-ray generating apparatus and transmitted through a subject; and a controlling apparatus which controls the X-ray generating apparatus and the X-ray detecting apparatus so that the X-ray generating apparatus and the X-ray detecting apparatus cooperate with each other.

23. A transmitting type target comprising:
an electrically insulating substrate having a pair of surfaces facing each other and an annular lateral periphery coupled with each of the pair of surfaces;
a target located on one of the pair of surfaces and located at an internal region internally spaced apart from the annular lateral periphery;
a first conductive member located on the one of the pair of surfaces and having an inner edge portion being overlapped to a peripheral of the target; and
a second conductive member provided on or underneath the target,
wherein the second conductive member has a thickness of 0.1 µm or less.

24. The transmitting type target according to claim 23, wherein the thickness of the second conductive member is 0.1 nm or more.

25. The transmitting type target according to claim 23, wherein the second conductive member overlaps the first conductive member.

26. The transmitting type target according to claim 25, wherein the second conductive member is located between the target and the one of the pair of surfaces of the electrically insulating substrate.

27. An X-ray generating apparatus comprising the transmitting type target according to claim 23 and an electron emitting source facing the transmitting type target.

28. A radiography system comprising:
the X-ray generating apparatus according to claim 27;
an X-ray detecting apparatus which detects an X-ray emitted from the X-ray generating apparatus and transmitted through a subject; and
a controlling apparatus which controls the X-ray generating apparatus and the X-ray detecting apparatus so that the X-ray generating apparatus and the X-ray detecting apparatus cooperate with each other.

* * * * *